United States Patent [19]
Seldin

[11] Patent Number: 5,672,177
[45] Date of Patent: Sep. 30, 1997

[54] IMPLANTABLE BONE DISTRACTION DEVICE

[75] Inventor: Edward B. Seldin, Cambridge, Mass.

[73] Assignee: The General Hospital Corporation, Boston, Mass.

[21] Appl. No.: 594,157

[22] Filed: Jan. 31, 1996

[51] Int. Cl.$^6$ .................................................. A61B 17/58
[52] U.S. Cl. ................................................ 606/71; 606/105
[58] Field of Search .......................... 606/53, 54, 55, 606/57, 58, 69, 70, 71, 86, 87, 105, 74, 151

[56] References Cited

U.S. PATENT DOCUMENTS

| | | |
|---|---|---|
| 3,547,114 | 12/1970 | Haboush . |
| 3,604,414 | 9/1971 | Borges . |
| 3,659,595 | 5/1972 | Haboush ................................. 606/71 |
| 4,119,092 | 10/1978 | Gil . |
| 4,157,715 | 6/1979 | Westerhoff ............................. 606/60 |
| 4,246,660 | 1/1981 | Wevers ................................. 623/13 |
| 5,364,396 | 11/1994 | Robinson et al. . |
| 5,462,542 | 10/1995 | Alesi, Jr. ............................... 606/151 |

*Primary Examiner*—Michael Buiz
*Assistant Examiner*—David O. Reip
*Attorney, Agent, or Firm*—Lappin & Kusmer LLP

[57] ABSTRACT

An implantable bone distraction device for inducing controlled lengthening of at an osteotomy site. The device has two elongated plates which are operatively positioned to be substantially parallel and to overlap partially. Each of the plates includes a portion adapted for affixing the plates to respective bone segments. The first plate includes a plurality of parallel sawtooth ridges extending transverse from the long axis of the plate. The second plate includes at least one resilient pawl and at least one resilient ratchet arm. The pawl and arm are engageable with the ridges on the first plate. The ratchet arm responds to application of force on it by engaging with one of the ridges on the first plate and pushing the first plate away from the second plate in the direction of their common axes. The first bone segment is thus moved away from the second bone segment in the direction of the common axes of the plates in a controlled fashion. Backward movement of the first plate toward the second plate is prevented by the abutting engagement of the pawl with one of the ridges on the first plate.

8 Claims, 4 Drawing Sheets

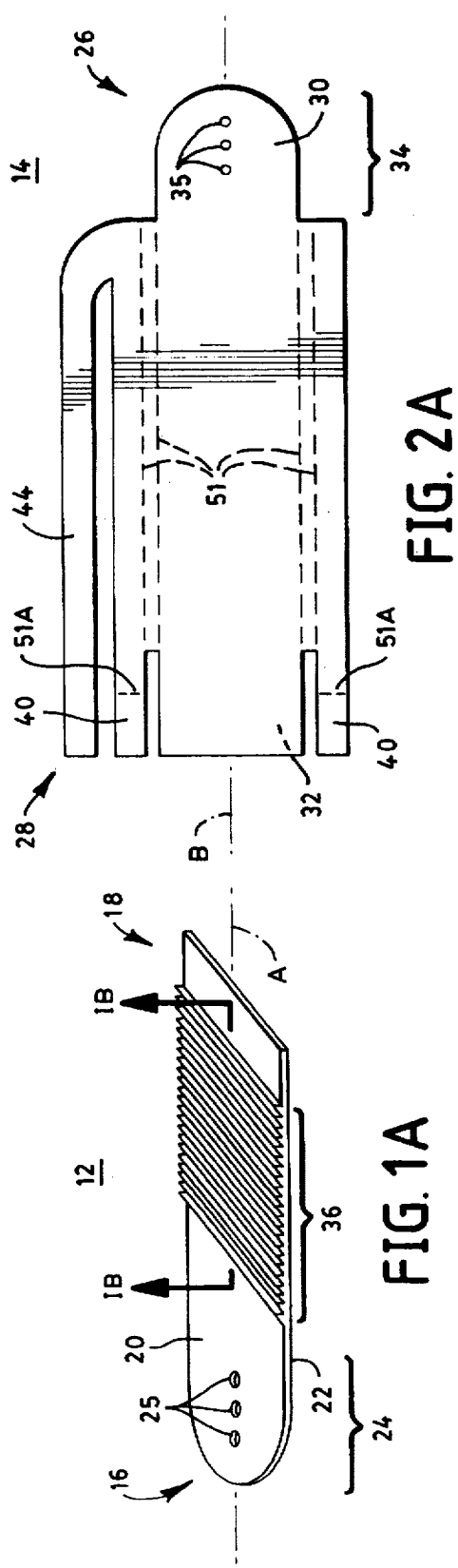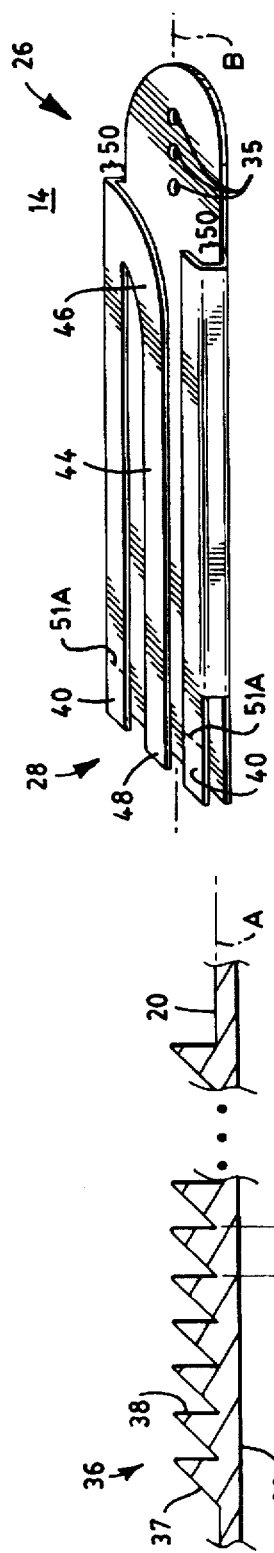

5,672,177

IMPLANTABLE BONE DISTRACTION DEVICE

FIELD OF THE INVENTION

The present invention relates to surgical devices used in distraction osteosynthesis to induce and control the lengthening of bones at the site of an osteotomy. More particularly, the invention relates to implantable bone distraction devices.

BACKGROUND OF THE INVENTION

Distraction osteosynthesis is a surgical procedure in which the natural reparative and regenerative properties of bone are employed to induce controlled lengthening of bone sections at the site of an osteotomy. The procedure is typically employed in corrective jaw and facial surgery, as well as in other types of reconstructive surgery.

Bone distraction devices are generally affixed to separate sections of bone on either side of an osteotomy with transcutaneous pins. The device may include other transcutaneous projections which are adapted for receiving external forces for adjusting the device from outside of the patient.

Because portions of the device extend through the patient's skin, the patient experiences great discomfort. Further, the pins are unsightly and cause unavoidable, sometimes severe, scarring, especially in areas of sensitive skin on the face and neck. Such consequences have been considered acceptable only because of the severity of the underlying conditions and the necessity for radical treatment.

A typical bone distraction device and method are disclosed in U.S. Pat. No. 5,364,596 to Robinson et al. The disclosed device comprises a pair of blocks, one defining a drive chamber and the other defining a threaded bore which receives a threaded, rotatable drive rod. The blocks have a relatively low profile to facilitate their subcutaneous implantation and attachment to bone sections on either side of an osteotomy. A percutaneous port projects outwardly from one of the blocks to permit adjustment of the device. A separate adjustment tool cooperates with a drive rod actuator to rotate the drive rod and adjust the spacing between the blocks to control the distraction process.

The Robinson et al. device is not totally implantable within the patient. The percutaneous port is unsightly and uncomfortable for the patient, and scarring at the site of the percutaneous port cannot be avoided.

It would be an advancement in the art to provide a bone distraction device which is wholly implantable within a patient and which can be adjusted as needed without reopening the osteotomy site or otherwise requiring the use of an invasive device or procedure.

SUMMARY OF THE INVENTION

According to one aspect of the invention, there is provided an implantable device for distracting first and second bone segments. The device comprises an elongated first plate which extends along a first axis between first and second ends, and an elongated second plate which extends along a second axis between first and second ends. Each of the plates has an upper surface and a lower surface. The first plate has a portion near its first end which is adapted for affixing the first plate to the first bone segment so that the lower surface of the first plate is adjacent to the first bone segment. The second plate has a portion near its second end which is also adapted for affixing the second plate to the second bone segment so that the lower surface of the second plate is adjacent to the second bone segment.

The device further includes an assembly for positioning the first and second plates so that they are parallel and overlap to the extent that at least the portion of the first plate that includes the second end is adjacent to at least the portion of the second plate that includes the first end. As positioned, the first and second axes of the respective plates are substantially parallel. The first plate is movable with respect to the second plate in the direction of the first and second axes.

The upper surface of the first plate includes a plurality of parallel saw-tooth ridges which extend transverse to the first axis. Each of the ridges includes a drive surface which extends from, and is substantially perpendicular to, the upper surface of the first plate. The drive surfaces of the ridges face the second end of the first plate.

The second plate includes at least one resilient pawl which extends from the first end of the second plate. The pawl is biased toward, and is engageable with, the ridges on the first plate. The second plate further includes at least one resilient, elongated, arcuate arm which has a proximal end and a distal end. The proximal end extends from the first end of the second plate, with its distal end extending toward and being engageable with the ridges on the first plate.

In one embodiment, the positioning assembly comprises at least one extension from the second plate, the extension forming a guide that is adapted for partially enclosing at least a portion of the first plate. In another embodiment, the positioning assembly comprises at least one extension from the first plate which forms a guide adapted for partially enclosing at least a portion of the second plate.

These and other features of the invention will be more fully appreciated with reference to the following detailed description which is to be read in conjunction with the attached drawings.

BRIEF DESCRIPTION OF THE DRAWINGS

The invention is further described by the following description and figures, in which:

FIG. 1A is a plan view of the first plate of the device according to one embodiment of the invention;

FIG. 1B is a section view of the first plate shown in FIG. 1, taken along section IB—IB;

FIG. 2A & 2B are a plan view of the second plate of the device according to the embodiment shown in FIG. 1;

Like elements in the respective FIGURES have the same reference numbers.

DETAILED DESCRIPTION OF THE PREFERRED EMBODIMENT

The bone distraction device of the present invention is wholly implantable within a patient and can be adjusted from outside the patient without reopening the osteotomy site and without requiring transcutaneous projections. The device includes two plates, each of which is engaged to a bone segment and which engage with one another. The device is configured so that the engaged plates may be operated in a ratcheting manner in response to the extracorporeal application of forces thereby effecting controlled lengthening of the device and thus inducing controlled lengthening of the bone segments to which the plates are attached.

Figure 3:
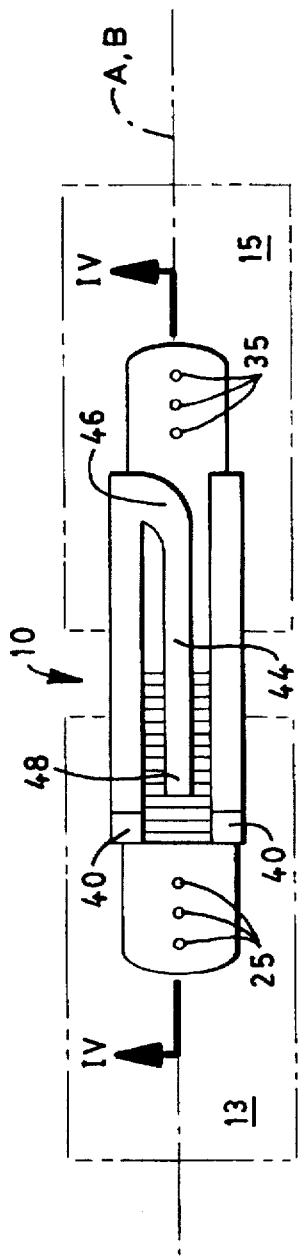
FIG. 3 is a plan view of the embodiment of the device of FIGS. 1 and 2, in which the first and second plates are operatively engaged.
Figure 4:
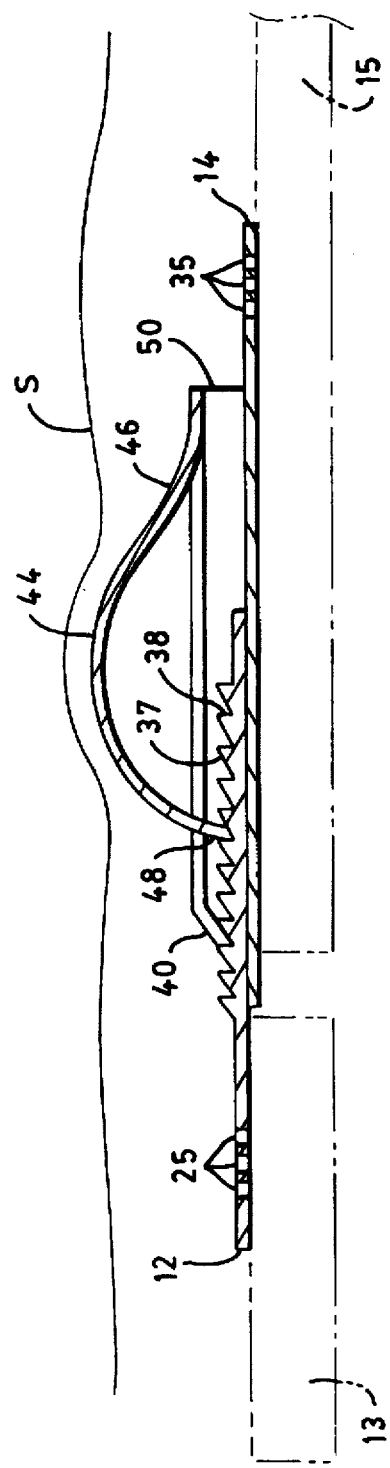
FIG. 4 is a sectional view of the device shown in FIG. 3, taken along section lines IV—IV.

A preferred form of the invention is shown as device 10 in FIGS. 1A–4. FIG. 4 shows the device 10 subcutaneously implanted beneath the skin S of a patient. The device 10 comprises a first elongated plate 12, as shown in FIG. 1A, and a second elongated plate 14, as shown in FIGS. 2A and 2B. The first elongated plate 12 extends along a first axis A between a first end 16 and a second end 18. The plate 12 has an upper surface 20 and a lower surface 22, and a portion 24 near the first end 16 of the plate adapted for affixing the plate 12 to a first bone segment 13 (shown in FIGS. 3 and 4) so that the lower surface 22 of the plate 12 is adjacent to the first bone segment. The upper surface 20 of the first plate 12 includes a plurality of parallel saw-tooth ridges 36, shown in detail in FIG. 1B. The ridges 36 extend transverse to the axis A of the first plate. Each ridge includes a sloped surface 37 and a drive surface 38, as shown. The drive surface 38 extends from, and is substantially perpendicular to, the upper surface 20 of the plate, and the sloped surface 37 is inclined with respect to the upper surface 20. The drive surfaces 38 of the ridges face the second end 18 of the first plate, and the sloped surfaces 37 face the first end 16. FIGS. 2A and 2B show a second plate 14 that is adapted for use with plate 12. In the illustrated embodiment, plate 12 is stamped from a sheet material to the form shown in FIG. 2A, and then folded along fold lines 51 to be in the form shown in FIG. 2B.

As shown in FIG. 2, the second plate 14 extends along a second axis B between a first end 26 and a second end 28. The second plate also has an upper surface 30 and a lower surface 32, and a portion 34 near the first end 26 adapted for affixing the second plate to a second bone segment 15 (shown in FIGS. 3 and 4) so that the lower surface 32 of the second plate 14 is adjacent to the second bone segment.

The second plate 14 includes two resilient pawls 40 which extend from the second end 28 of the second plate 14 and are bent along fold lines 51A (as shown in FIG. 3) toward upper surface 30. Although the illustrated embodiment includes two pawls, other embodiments may have a different number of pawls. Prior to implantation, the pawls 40 are bent along fold lines 51A toward upper surface 30, as shown in FIG. 3. The second plate 14 further includes at least one resilient, elongated ratchet arm 44. The proximal end 46 of the arm 44 joins the arm to the first end 26 of the plate 14, and the distal end 48 of the arm extends toward the distal end 28. When plates 12 and 14 are assembled to be a two-element device, the distal end 48 of arm 44 extends over the first plate 12 and towards the ridges 36, as will be more fully explained below. In the illustrated embodiment, as shown in FIGS. 2A and 2B, the arm 44 is planar, but before implantation, it is imparted with a curvature, for example, to have the general shape shown in FIG. 4, so that end 48 will engage one of the ridges 36 when device 10 is assembled.

The portions 24, 34 of the respective plates 12, 14 which are adapted for affixing the plates to bone segments 13, 15 include sets of holes 25, 35 in the respective plates which are adapted for receiving threaded bone screws, pins or fasteners (not shown), or other securing devices suitable for use in anchoring the plates to bone.

The device further includes an assembly 50 for supporting the plates together so that their principal planes are substantially parallel and their respective axes A and B are substantially parallel, as shown in FIG. 3, and plate 12 is slidingly positioned (in the direction of axes A, B) with respect to plate 14. The positioning assembly 50 restricts movement of the first plate 12 to movement only in the direction of the axes A and B. In one embodiment, the positioning assembly 50 comprises at least one extension from the second plate which is adapted to form a guide or channel for partially enclosing at least a portion of the first plate 12. In another embodiment, the positioning assembly 50 comprises at least one extension from the first plate which is adapted to form a guide or channel for partially enclosing at least a portion of the second plate.

In the positioning assembly 50, the plates 12, 14 overlap so that at least the portion of the first plate 12 that includes the second end 18 of that plate is adjacent to at least the portion of the second plate 14 that includes the first end 26 of that plate.

In the embodiment of the invention illustrated in FIGS. 1A–4, the second plate 14 is made of a unitary construction. The positioning assembly 50 in this embodiment comprises a pair of extensions from a central portion of the second plate 14. The extensions are formed along fold lines 51 into a guide channel for partially enclosing the first plate 12, as shown in FIGS. 2B and 3.

Figure 5:
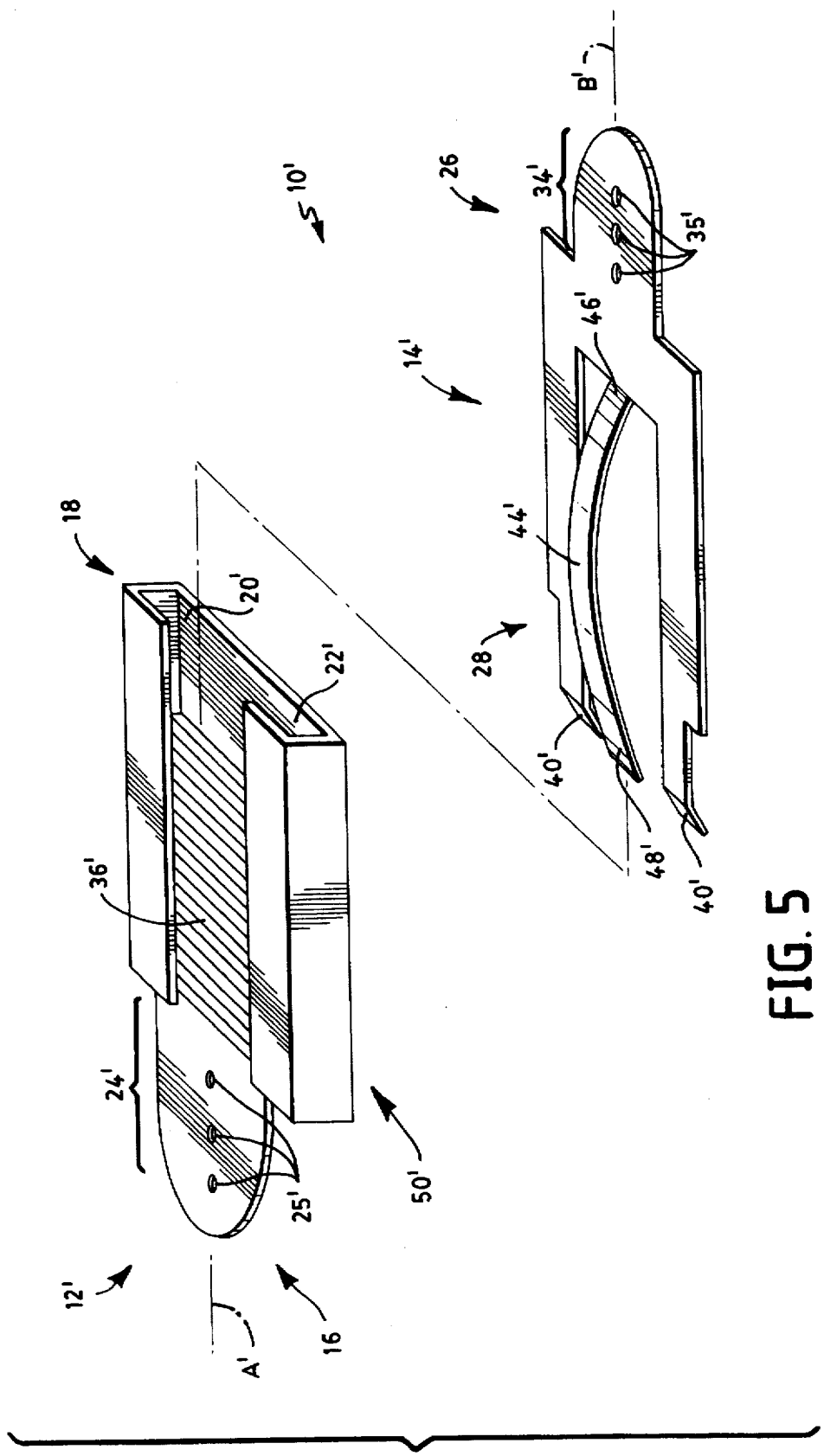
FIG. 5 is an exploded perspective view of another embodiment of the invention.

An alternative form of the invention is shown as device 10' in FIG. 5. The device includes two elongated plates 12' and 14' extending along respective axes A', B'. The first plate 12' includes an upper surface 20' and a lower surface 22' and a portion 24' near the first end adapted for affixing the first plate to a first bone segment (not shown) so that the lower surface 22' is adjacent to the first bone segment. The second plate 14' also includes an upper surface 30' and a lower surface 32' and a portion 34' near the first end which is adapted for affixing the second plate to a second bone segment (not shown) so that the lower surface 32' is adjacent thereto.

The upper surface 20' of the first plate 12' includes a plurality of sawtooth ridges 36' extending transverse to the axis A', as in the embodiment of FIGS. 1A–4. Each ridge includes a sloped surface 37' which is inclined relative to the upper surface 20', and a drive surface 38' which is substantially perpendicular to the upper surface 20' of the first plate. As in the embodiment of FIGS. 1A–4, the drive surfaces 38' face the second end of the first plate and the sloped surfaces 37' face the first end.

Portions 24', 34' of the respective plates 12', 14' are adapted with holes 25', 35' for affixing the respective plates to respective bone segments 13, 15 (not shown) with threaded bone screws, pins, fasteners (not shown), or other suitable securing devices, as in the embodiment of FIGS. 1A–4.

In the embodiment of FIG. 5, the first plate 12' includes a positioning assembly 50', which comprises a pair of extensions from either side of a central portion of the first plate. As with the embodiment of FIGS. 1A–4, the extensions can be formed into a guide channel for receiving and partially enclosing at least a portion of the second plate 14', as explained more fully below.

The second plate 14' includes at least one, and preferably a pair of, resilient pawls 40' which extend from the end of 28' the second plate, as in the embodiment of FIGS. 1A–4. The second plate further includes an elongated, resilient, ratchet arm 44' extending from the first end 26' of the second plate. The lateral edges of plate 14' are adapted to fit within the guide channels formed from the extensions of the first plate 12', and, when assembled, the ratchet arm 44' engages with the ridges 36' between the channels so formed, as shown in FIG. 5.

The plates 12, 12', 14, 14' are preferably made of a biocompatible material, such as, for example, titanium or vitallium, which is suitable for implantation in a patient. Alternatively, the plates can be constructed of a biodegradable material which is designed to break down over time in the body and be absorbed into the surrounding tissues and/or excreted as waste.

In use, the device 10 is first implanted under the patient's skin S over the two bone segments 13, 15 which are to be distracted by a predetermined distance. The plates 12, 14 of the device are then affixed to the respective bone segments 13, 15 with bone screws or the like at holes 25, 35. The osteotomy site is then closed.

To distract the bone segments 13, 15, a succession of forces is applied through the skin to the ratchet arm 44 of the device. In response to these forces, the device 10 operates with a ratcheting action that permits the controlled lengthening of the device in the direction of the first and second axes A, B and thus of the bone segments 13, 15 affixed to the respective plates 12, 14.

Figure 6A:
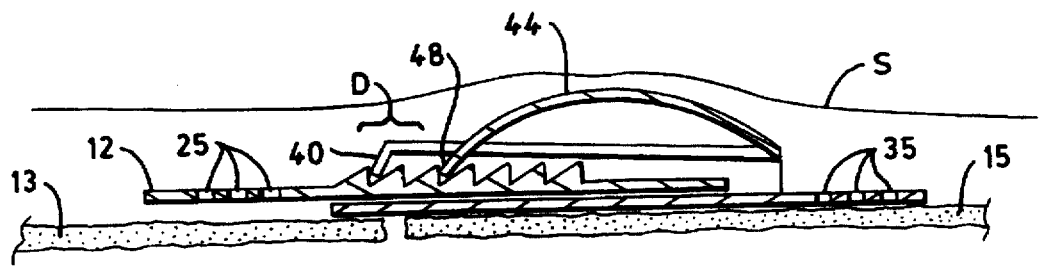
FIGS. 6A–6C are sequential schematic representations of the device of FIG. 1 in use in distracting two bone segments.
Figure 6B:
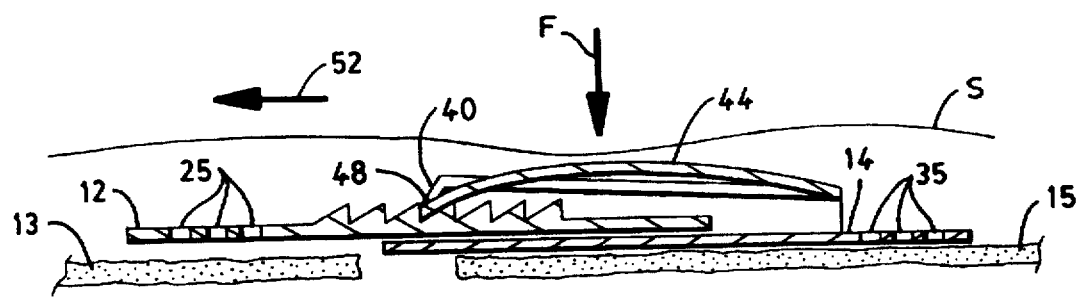
Figure 6C:
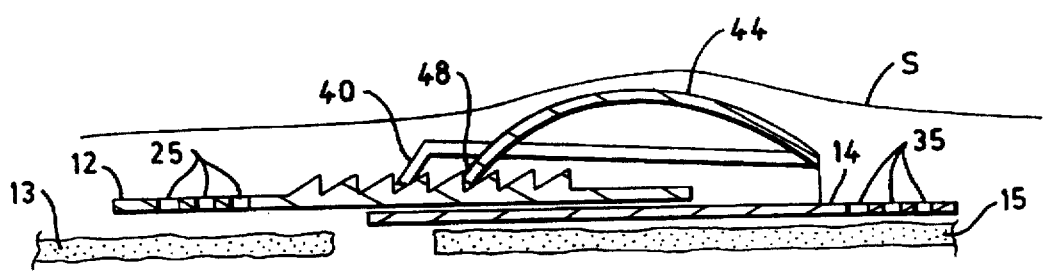

FIGS. 6A–6C schematically illustrate the device 10 as implanted under the skin S of a patient and in operation. The first plate 12 includes eight transverse ridges 36 and spaced apart by a distance D, equal to the pitch of the ridges on the plate. A ridge which is forward (i.e., to the left in FIGS. 6A–6C) of the ratchet arm 44 and pawl 40 is designated as a "leading" ridge, and a ridge which is rearward (i.e., to the right in the FIGURE) of the ratchet arm 44 and pawl 40 is designated as a "trailing" ridge. A ridge which is engaged by the resilient pawl is designated as the "engaging" ridge. As shown, the second plate 14 includes one resilient pawl 40 and a ratchet arm 44 extending from the first end of the second plate. The ratchet arm 44 extends over the first and second plates 12, 14 to a point near the ridges on the first plate. The arm 44 includes a distal end 48 which is adapted for engagement with the ridges on the first plate. The resilient pawl 40 at its distal end is also adapted for engagement with the ridges on the first plate. The plates 12, 14 are positioned so that their axes A, B are substantially parallel and so that the plates overlap to the extent that at least the portion of the first plate that includes the second end is adjacent to the portion of the second plate that includes the first end.

Initially, as shown in FIG. 6A, the plates are stationary with respect to each other, and the distal finger end of the resilient pawl 40 abuts against a drive surface of the leftmost engaging ridge to prevent the first plate 12 from moving toward the second plate 14. In the absence of any appreciable downward force on the ratchet arm 44, that arm is in a relaxed state with its distal end 48 located generally between the third and fourth engaging ridges, as shown in FIG. 6A.

In FIG. 6B, a downward force F is applied through the patient's skin S to the ratchet arm 44. That force depresses the arm and causes it to elongate in the direction of its free end 48, i.e., toward the first end of the first plate in the direction of arrow 52. The distal end 48 of the arm 44 abuts against a drive surface 38 of the third ridge on the first plate, and the force thus applied to the arm 44 pushes the first plate 12 away from the second plate 14 along the axes A and B. In the illustrated example, the force establishes relative motion between plates 12 and 14 in the amount of 2D (i.e., two ridges). The distal end of the resilient pawl 40 overrides the sloped surface 37 of the second and third ridge as the first plate 12 moves away from the second plate 14. The device 10 is thereby lengthened by distance 2D, and the bone segments 13, 15 affixed to the respective plates 12, 14 are distracted by distance 2D along the common axes A, B. After that motion of plate 12 relative to plate 14 is established, the pawl 40 is biased against the drive surface of the third ridge, preventing motion in a direction opposite to arrow 52.

In FIG. 6C, the plates 12, 14 are stationary relative to each other as in FIG. 6A. The absence of force on the arm 44 relaxes the arm to its rest state, and the distal tip 48 of the arm 44 rests between the fifth and sixth ridges. The distal finger end of the resilient pawl 40 engages with drive surface 38 of a now-engaging ridge and thus prevents backward movement of the first plate 12 toward the second plate 14.

Subsequent applications of force on the arm 44 advance the first plate 12 away from the second plate 14 along the common axes A, B in a ratcheting motion along the ridges of the first plate, as previously described. Backward movement of the first plate 12 toward the second plate 14, and thus of the first bone segment 13 toward the second bone segment 15, is prevented by the abutting engagement of the pawls 40 with the driving surface 38 of the ridge with which the distal end 48 of the arm 44 was previously engaged.

Thus, the device can be actuated to induce bone distraction by, for example, digital application of force on the skin immediately overlying the device. Such action depresses the arm 44 and moves the first plate 12 away from the second plate 14 as previously described. Alternatively, the device can be activated magnetically by energizing an electric circuit (not shown) associated with the device and transmitting one or more electric pulses to an electromagnetic relay to depress the arm and effect movement of the first plate relative to the second plate. Other means for directly or remotely activating the device by application of pressure on the arm can also be used.

The device can be made in a wide variety of shapes and sizes to accommodate any type of reconstructive surgery or bone distraction requirements. For example, the plates can extend along axes which are curvilinear in order to permit distraction of bone segments attached thereto in a curvilinear direction around predetermined centers of rotation. The plates can alternatively be constructed to incorporate compound shapes to induce various combinations of linear and curved bone growth. Further, the plates can be designed to include preselected angles, or they can be adjusted to produce a desired growth angle, to induce bone distraction according to a predetermined geometry. In a preferred embodiment, the plates of the device can be fabricated from sheet metal stock which can be easily folded to form the enclosing portion of the device; however, other fabrication modes, such as, for example, fabrication by casting or machining or other known methods, are considered to fall within the scope of the invention.

The bone distraction device of the present invention is highly advantageous for use in bone distraction surgery, because it is wholly implantable within the patient and can be easily adjusted from outside the patient. Scarring and the potential for infection due to the presence of unsightly and uncomfortable transcutaneous pins are eliminated. Bone distraction is easily effected by mere application of force on the ratchet arm of the device through the patient's skin, without the need for reopening the osteotomy site.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

I claim:

1. An implantable device for distracting first and second bone segments, comprising:
   A. an elongated first plate extending along a first axis between first and second ends thereof, said first plate having an upper surface and a lower surface, and having means near said first end for affixing said first plate to said first bone segment whereby said lower surface of said first plate is adjacent to said first bone segment;
   B. an elongated second plate extending along a second axis between first and second ends thereof, said second plate having an upper surface and a lower surface, and having means near said first end for affixing said second plate to said second bone segment whereby said lower surface of said second plate is adjacent to said second bone segment;
   C. and means for positioning said first and second plates to be slidingly engaged, with at least the portion of said first plate including said second end being adjacent to at least the portion of said second plate including said first end, whereby said first and second axes are substantially parallel, and whereby said first plate is movable with respect to said second plate in the direction of said first and second axes;

wherein said upper surface of said first plate includes a plurality of parallel saw-tooth ridges extending transverse to said first axis, each of said ridges including a drive surface, said drive surface extending from, and being substantially perpendicular to, said upper surface of said first plate and facing said second end of said first plate, wherein said second plate comprises at least one resilient pawl extending from said first end of said second plate, said pawl being biased toward and engaging with one of said ridges, and wherein said second plate further comprises at least one resilient elongated ratchet arm having a proximal end extending from said first end of said second plate and a distal end extending toward and engaging with one of said ridges.

2. A device according to claim 1, wherein said means for affixing said plates to said bone segments comprises a plurality of bone screws for threading into each of said bone segments through a plurality of holes in each of said plates.

3. A device according to claim 1, wherein said arm and said pawl are adapted for engagement with a drive surface on one of said ridges on said first plate.

4. A device according to claim 3, wherein application of force on said arm causes said arm to engage with said drive surface, thereby moving said first plate away from said second plate along said axes, and wherein release of force on said arm causes said arm to disengage from said drive surface and causes said pawl to engage with said drive surface, thereby preventing movement of said first plate toward said second plate.

5. A device according to claim 1, wherein said plates are made of a biocompatible material.

6. A device according to claim 5, wherein said plates are made of a biodegradable material.

7. A device according to claim 1, wherein said positioning means comprises at least one extension from said second plate, wherein said extension forms a guide for partially enclosing at least a portion of said first plate.

8. A device according to claim 1, wherein said positioning means comprises at least one extension from said first plate, wherein said extension forms a guide for partially enclosing at least a portion of said second plate.

* * * * *